(12) United States Patent
Wang (10) Patent No.: US 6,652,575 B2
(45) Date of Patent: *Nov. 25, 2003

(54) STENT WITH SMOOTH ENDS

(75) Inventor: Lixiao Wang, Maple Grove, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/017,004

(22) Filed: Dec. 14, 2001

(65) Prior Publication Data

US 2002/0055769 A1 May 9, 2002

Related U.S. Application Data

(63) Continuation of application No. 09/374,425, filed on Aug. 13, 1999, now Pat. No. 6,379,379, which is a continuation of application No. 09/072,944, filed on May 5, 1998, now abandoned.

(51) Int. Cl.[7] ............................... A61F 2/06; A61F 2/09
(52) U.S. Cl. ..................................... 623/1.15; 623/1.42
(58) Field of Search ............................... 623/1.15, 1.31, 623/1.46, 1.42; 427/2.1–2.31

(56) References Cited

U.S. PATENT DOCUMENTS

| | | | |
|---|---|---|---|
| 4,503,569 A | 3/1985 | Dotter | |
| 4,512,338 A | 4/1985 | Balko et al. | |
| 4,728,328 A | * 3/1988 | Hughes et al. | 623/12 |
| 4,732,152 A | 3/1988 | Wallsten et al. | |
| 4,733,665 A | 3/1988 | Palmaz | |
| 4,848,343 A | 7/1989 | Wallsten et al. | |
| 5,019,090 A | 5/1991 | Pinchuk | |
| 5,064,435 A | * 11/1991 | Porter | 623/1 |
| 5,213,580 A | 5/1993 | Slepian et al. | |
| 5,234,457 A | 8/1993 | Andersen | |
| 5,318,531 A | 6/1994 | Leone | |
| 5,342,300 A | 8/1994 | Stefanadis et al. | 604/95 |
| 5,383,892 A | 1/1995 | Cardon et al. | 606/198 |
| 5,385,935 A | * 1/1995 | Tamai et al. | 514/535 |
| 5,443,500 A | 8/1995 | Sigwart | |
| 5,449,373 A | 9/1995 | Pinchasik et al. | |
| 5,500,013 A | 3/1996 | Buscemi et al. | |
| 5,514,154 A | 5/1996 | Lau et al. | |
| 5,540,712 A | 7/1996 | Kleshinski et al. | |
| 5,562,922 A | * 10/1996 | Lambert | 424/486 |
| 5,624,411 A | 4/1997 | Tuch | |
| 5,628,785 A | 5/1997 | Schwartz et al. | |
| 5,658,308 A | 8/1997 | Snyder | 606/191 |
| 5,667,523 A | * 9/1997 | Bynon et al. | 623/1 |
| 5,693,085 A | 12/1997 | Buirge et al. | |
| 5,713,949 A | 2/1998 | Jayaraman | |

(List continued on next page.)

FOREIGN PATENT DOCUMENTS

| | | |
|---|---|---|
| EP | 0 716 836 A1 | 6/1996 |
| EP | 0 723 766 A1 | 7/1996 |
| EP | 0 740 928 A2 | 11/1996 |

OTHER PUBLICATIONS

Tao Peng et al., "Role of Polymers in Improving the Results of Stenting in Coronary Arteries", Biomaterials 1996, vol. 17 No. 7, pp. 685–691, Dec. 1994.*

*Primary Examiner*—David H. Willse
*Assistant Examiner*—Suzette J. Jackson
(74) *Attorney, Agent, or Firm*—Pennie & Edmonds LLP (57) ABSTRACT

A stent having at least one smooth end is disclosed. The stent may include a coating or coatings on one or both end portions to provide a smooth finish to reduce possible damage to body passages when the stent is deployed and delivered. The stent may also contain drugs or surgical adhesives or a combination thereof in or on the coated portion of the stent. The stent may also be of the type where the materials of the stent may be treated to have a smooth flexible end or ends. The stent may also be of a configuration such that at least one end is more flexible than the middle portion of the stent.

16 Claims, 6 Drawing Sheets

U.S. PATENT DOCUMENTS

| | | | |
|---|---|---|---|
| 5,716,393 A | | 2/1998 | Lindenberg et al. |
| 5,725,572 A | * | 3/1998 | Lam et al. ................ 623/1.15 |
| 5,741,333 A | | 4/1998 | Frid |
| 5,746,691 A | * | 5/1998 | Frantzen ...................... 600/36 |
| 5,749,919 A | | 5/1998 | Blanc ............................. 623/1 |
| 5,755,769 A | | 5/1998 | Richard et al. ............... 623/11 |
| 5,788,626 A | * | 8/1998 | Thompson ..................... 623/1 |
| 5,800,520 A | | 9/1998 | Fogarty et al. ................ 623/1 |
| 5,807,404 A | | 9/1998 | Richter .......................... 623/1 |
| 5,817,126 A | * | 10/1998 | Imran ......................... 606/198 |
| 5,824,037 A | * | 10/1998 | Fogarty et al. ................ 623/1 |
| 5,824,049 A | * | 10/1998 | Ragheb et al. ................. 623/1 |
| 6,106,548 A | * | 8/2000 | Roubin et al. ............. 623/1.15 |
| 6,168,619 B1 | * | 1/2001 | Dinh et al. ................ 623/1.13 |
| 6,254,632 B1 | * | 7/2001 | Wu et al. .................. 623/1.15 |
| 6,379,379 B1 | * | 4/2002 | Wang ........................ 623/1.15 |
| 6,485,509 B2 | * | 11/2002 | Killion et al. ............. 623/1.15 |
| 6,488,701 B1 | * | 12/2002 | Nolting et al. ............. 623/1.13 |

\* cited by examiner

STENT WITH SMOOTH ENDS

This is a continuation of application Ser. No. 09/374,425, filed Aug. 13, 1999, now U.S. Pat. No. 6,379,379, which is a continuation of application Ser. No. 09/072,944, filed May 5, 1998, now abandoned.

FIELD OF THE INVENTION

This invention relates to a stent for use in body passages and more particularly, to a stent having at least one end which is coated or to a stent having at least one end which is treated to be smooth and flexible. The invention also has particular relevance to a stent having at least one end coated where the coating consists at least in part of drugs for delivery.

BACKGROUND OF THE INVENTION

Stents are used in human or animal body passages for maintaining the patency of the passages. Stents are generally tubular in configuration, open ended and are expandable between a generally unexpanded insertion diameter and an expanded implantation diameter. Stents are commonly placed or implanted by a mechanical transluminal procedure.

Prior art patents refer to the construction and design of stents as well as apparatus for positioning stents within a vessel or other passage. In general, for example, such patents disclose a technique for positioning an elongated cylindrical stent at a region of stenosis, an aneurysm, or the like. The stent expands as necessary to an implanted configuration after insertion with the aid of a catheter.

Specifically, U.S. Pat. No. 4,733,665 to Palmaz discloses a number of stent configurations for implantation with the aid of a catheter. U.S. Pat. No. 5,019,090 to Pinchuk discloses a generally cylindrical stent and technique for implanting it using a deflated balloon catheter to position the stent. U.S. Pat. No. 4,503,569 to Dotter and U.S. Pat. No. 4,512,338 to Balko et al. disclose a spring stent and a shape memory alloy stent. There are also self-expanding stents such as those described in U.S. Pat. No. 4,732,152 to Wallsten et al. and U.S. Pat. No. 4,848,343 to Wallsten et al. All of these patents are hereby incorporated by reference.

It is important that the placement of the stent not contribute to or cause additional blocking. It is known that when stents are expanded to their implantation diameter the ends of the stent may press into the vessel or cavity walls, especially the distal end of the stent. The sharp or pointed edges and ends of some stents may then damage the walls. Once damage has occurred, there is a likelihood that restenosis will occur at these points where the stents ends and edges have penetrated or pressed against the walls.

It is also known that stents may tear a passage wall and contribute to restenosis. This is particularly important for use of stents in blood vessels. A tear in the vessel wall may cause blockage of the vessel. When the wall is torn a flap of tissue is created. The torn wall or flap usually is the source of the blockage. The flap falls into the passage and blocks it. It is then necessary to perform another procedure to remove the blockage and generally, another stent is needed to open the vessel or other passage.

Restenosis occurs in a number of cases where a stent has been used. Tearing of the wall of the passage or injury of the endothelial cell layer are possible causes of the restenosis. Therefore, it is desirable to utilize a stent which reduces the chances of a damaged vessel wall or body passage which leads to further problems and further necessary procedures. However, current stents are not designed to reduce the occurrence of cutting of vascular passages or the like.

In addition, it is known that a number of drugs may reduce the chance of restenosis. Therefore, the use of these drugs in combination with a stent designed to reduce damage to body passages would be advantageous. However, known stents are not utilizing drugs with a means for reducing damage to vessels and the like.

It is also known that bioadhesives may be used to repair tissue walls which may have been torn. However, current stents are not designed to avert a potential problem due to a tear. Currently, stents are not utilizing a bioadhesive with a stent to repair tissue walls and prevent further medical procedures required because of the dissection of a body passage.

Consequently, a need remains for a stent which reduces the chances of a tear or other damage of a body passage and which lessens the chances of further required procedures. The present invention provides a stent which reduces the limitations of the prior stents with regard to possible tearing and the need for further treatment and therefore, performs in an improved fashion.

SUMMARY OF THE INVENTION

In accordance with a preferred embodiment of this invention a stent is characterized in that it includes at least one end coated with a desired material or materials. The coating may be of any desirable type which lessens the chance of a tear in the passage, generally a coating with a smooth finish is preferred. Generally, any prior art stent may be improved by providing it with a coating layer or layers of polymeric composition on at least one end to provide a smooth finish. For another type, a stent may be provided with a sleeve which may be connected to one or both ends of the stent.

In another embodiment, the stent which has been coated or the stent which utilizes a sleeve may include bioadhesives and/or drugs to be delivered to the site where the stent is implanted. It is known that bioadhesives can be used to repair tissue walls. It is therefore desirable to utilize a polymer coating to carry and deliver a bioadhesive to the stent implantation location. In this manner, a potential problem can be averted by the presence of the bioadhesive in the case of a tear or dissection. It is further known that a number of different drugs can be useful if delivered to the stent site. It is desirable to deliver the drug or drugs with the stent when implantation is occurring or has occurred.

For yet another embodiment of the invention a stent is characterized in that at least one end is constructed in a manner such that the end is treated to be smooth and flexible. The stent material may be heat treated, for example, or the design of the stent may be such that it provides for flexibility on an end. Another embodiment includes a stent designed such that a looser mesh or pattern is utilized on the end or ends of the stent and a tighter mesh or pattern is utilized in the middle portion of the stent. These stents may also be coated on one or both ends as well as materially treated.

Yet another embodiment of the invention a stent is constructed of varying materials having different degrees of flexibility. A more rigid material is used in the center portion of the stent and a more flexible material is used for one or both of the end portions of the stent. This embodiment may also be materially treated to increase smoothness or flexibility and may also be coated.

Stents according to the invention may be self-expanding or of the type which are expandable from a reduced diameter configuration by an exterior force (as opposed to self-expanding). The expandable stents may be balloon expanding for example. Both types of stents are well known in the art and need not be described in additional detail herein.

Stents according to this invention may be metal stents or polymeric stents, the stent providing the basic framework for the device.

These and other advantages and features which characterize the invention are pointed out with particularity in the claims annexed hereto and which form a further part hereof. However, for a better understanding of the invention, its advantages and objects obtained by its use, reference should be made to the drawings which form a further part hereof, and the accompanying detailed description in which there is shown and described an illustrative embodiment of the invention.

BRIEF DESCRIPTION OF THE FIGURES

Referring to the drawings, wherein like numerals represent like parts throughout the several views.

DETAILED DESCRIPTION OF THE INVENTION

One embodiment of the invention contemplates the use of a metal or polymer stent which can have any configuration and may be any stent taken from the prior art or any other stent. This stent is coated on at least one end with an appropriate biocompatible coating to provide for a smooth end and edge.

Figure 1:
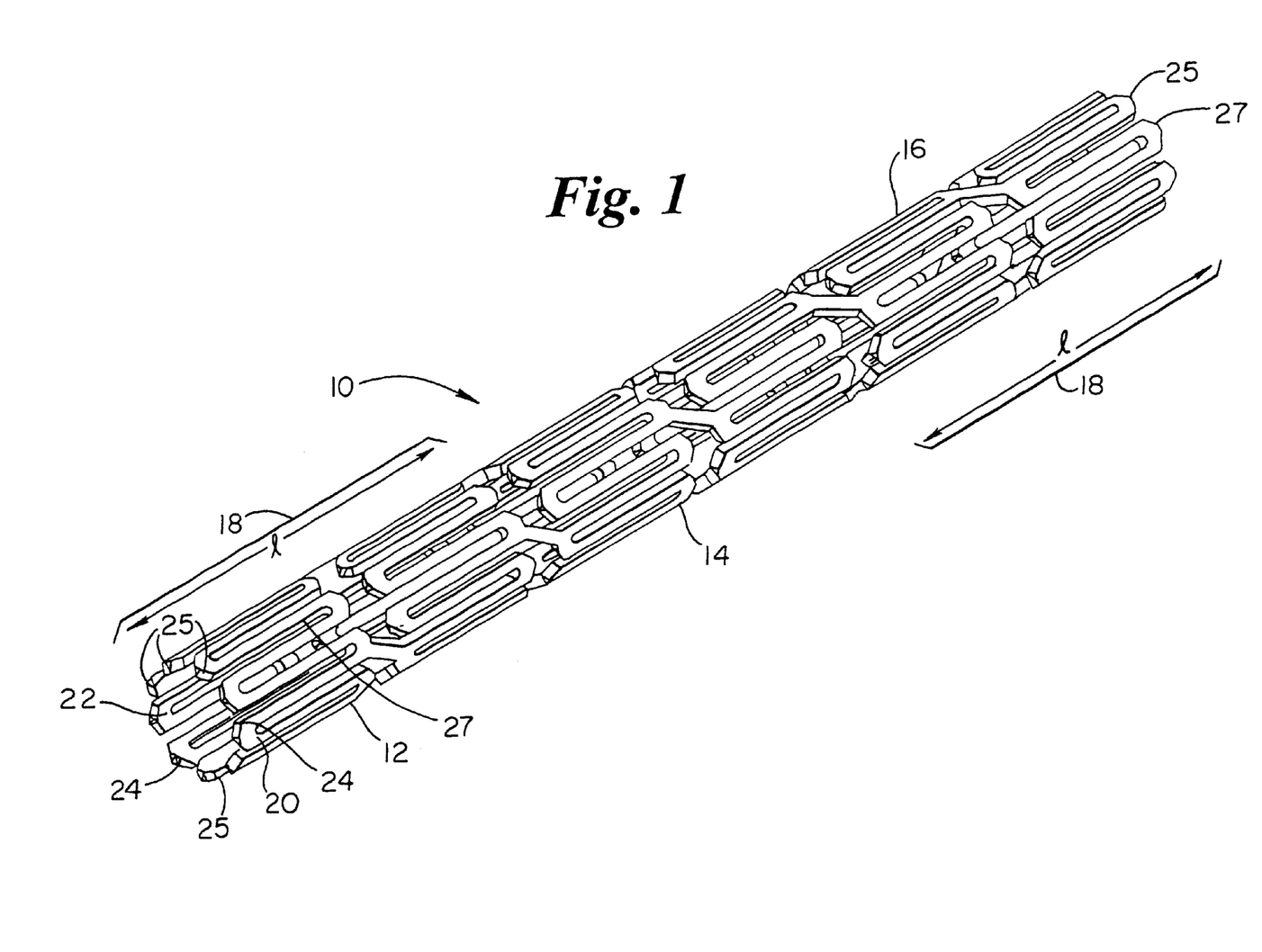
FIG. 1 is a perspective view of a stent according to the present invention.

Referring now to FIG. 1, a metal stent 10 is shown having a first end portion 12, a middle portion 14 and a second end portion 16. The stent 10 may be stainless steel or any other metal or material as is known in the art. In a preferred embodiment, the stent 10 includes a coating 18. The coating 18 is a biocompatible coating and has characteristics such as a smooth surface and flexibility for better performance. The coating may be permanent or biodegradable. Most biodegradable coatings degrade in the body within a few hours to a few years thereby serving the purpose of preventing tears during angioplasty or deployment. In a preferred embodiment the coating 18 is polytetrafluoroethylene (PTFE or TEFLON) or polyethylene oxide. Many other suitable coatings may be used with the invention. The following is an exemplary list of coatings:

Hydrophilic polymer coatings, copolymers (block or graft) or their crosslinked versions (e.g. hydrogels), the polymers including:

poly(hydroxyethyl methacrylate) and derivatives; poly (vinyl alcohol);

polyethylene oxide; polyethylene glycol; poly(propylene oxide);

polyacrylamides; polyacrylic acid; polymethacrylic acid; poly(N-vinyl-2-pyrollidone); hydrophilic polyurethanes; poly(aminoacid); water soluble cellulosic polymers (sodium carboxymethyl cellulose, hydroxyethyl cellulose, for example); collagens; carrageenan; alginate; starch; dextrin; gelatins;

Biodegradable Polymers;

poly(lactide); poly(glycolide); polydioxanone(PDS); polycaprolactone; polyhydroxybutyrate(PHBT); poly (phospazene); poly(phosphate ester); poly(lactide-co-glycolide); poly(glycolide-cotrimethylene carbonate); poly(glycolide-co-caprolactone); polyanhydrides;

Permanent Coatings:

polytetrafluoroethylene(PTFE); polyurethanes; polyamides; polyesters; polyethers; polyketones; polyether ester elastomers; polyether amide elastomers; polyacrylate-based elastomers; polyethylene; polypropylene.

This list is exemplary only. Any appropriate coating may be used.

Placing the coating or layer(s) 18 on the stent 10 may be done by any appropriate method such as dipping, painting, or spraying as is known in the art. The thickness of the coating can be varied as desired to achieve different affects and if the material is biodegradable to last for different desired periods of time. An exemplary range of thicknesses is about 0.01–0.32 mm. The thickness chosen depends on the materials used and the desired results. The thickness of the coating may vary. For example, the end of the stent may have a greater thickness than that on the outer surface of the stent. This may provide more of a buffer between the stent end and edge and the passage where may be needed the most. It is contemplated that one or more layers of coating may be applied by appropriate known methods. The layers of coating may be the same or may be coatings of different materials. Any appropriate coating materials may be combined as desired.

The coating 18 is applied to at least the first end portion 12 of the stent 10. If desired, the coating 18 may also be applied to the second end portion 16. The middle portion of the stent 10 remains uncoated in the present invention. Generally, it is more important to coat the distal end of the stent. This distal end is the end that first enters or engages the passage where the stent is needed. It is important that the stent not injure or tear the vessel wall as it is delivered to the problem area. The coated stent provides for a smooth stent portion to reduce the chances of damage. It is sometimes desirable to coat the proximal portion of the stent instead of or in addition to the distal end. The same or different biocompatible coating or coatings may be used to coat the distal and proximal ends.

The stent end portion or end portions may be coated on the outside surface 20, the inside surface 22, the side surface or surfaces 27, the end or ends 24 or the edge or edges 25. Depending on the configuration, the stent may have one or more end or side surfaces and one or more edges 25. A stent of such a configuration is shown in FIGS. 1–5, for example. The edges are created where two surface areas of the stent intersect such as the outer surface and the end surface; two end surfaces; or an end surface and a side surface, for example. The edges that are coated may include any of the edges in an end portion of the stent. It should be understood that any one or any combination of these surfaces 20, 22, 24, 25, and 27 may be coated. Generally, it is desirable to coat at least the end surface or surfaces 24 and the edge or edges 25 most proximate to the ends 24. In order to ensure that the coating adheres to the edge 25 of the stent at least a minimal portion of the outside or inside surface may also be coated. The coatings may cover any single area or combination of areas desired. When coating the outside, inside, edge and/or side surfaces 20, 22, 25 and 27, a varying portion of the length of the stent may be covered (length illustrated by 1 in FIG. 1). When coating one end portion of the stent, such as the distal end portion for example, anywhere from about 1% to 40% of the total stent may be coated. When coating both the distal and proximal end portions of the stent anywhere from about 2% to 80% of the stent may be coated. The length of the stent end portion(s) that is (are) coated will depend on a number of factors including the coatings used, results desired, stent application, etc.

The coating 18 may be applied such that a solid layer of coating covers the stent end portion (similar to FIG. 11) or the coating may have apertures or perforations which may or may not coincide with the pattern of the stent (similar to FIGS. 1–10).

The coating 18 may also be used as a drug delivery system to prevent restenosis or for other treatment. The drugs may include radiochemicals to irradiate and prohibit tissue growth. Angioplasty and stent deployment may cause injury of the endothelial cell layer of blood vessels, causing smooth muscle cell proliferation, leading to restenosis. To control smooth muscle cell growth endothelialization of cells on the inner wall surface of vessels will prevent or prohibit the smooth muscle growth. To stimulate endothelialization without provoking smooth muscle cell proliferation human growth factors may be included in the outer layer and delivered. Growth factors include VEGF, TGF-beta, IGF, PDGF, FGF, etc. These growth factors are dispersed in the matrix of the outer polymer coating 18 of the stent. All such materials are referred to herein generally as "drugs".

For carrying drugs, a gel-like material may be used. It may be applied over the coating 18 or directly to the stent 10 and used as the coating 18. There are two ways to apply drugs to such materials. The first way is to mix the drug with the materials, then coat the mixture onto the stent. They can be cast as film or sheet with drug together, then laminate to the core stent. A second way is to coat or laminate polymer with the core stent without the drug. The stent device is made, then sterilized. Due to their gel-like nature, the stent can then be inserted into a drug solution. The drug will be absorbed into/onto the gel. The stent can then be delivered into the body. The drug will then be released.

In one embodiment of the invention, the polymeric layer or coating 18 may be polyethylene oxide containing Taxol. Other coatings that may be used with a drug may be polymers such as PGA/PLA, PEO/PLA or the like containing a drug such as Taxol or hydrogen peroxide.

Preferred gel like materials for use as a coating for the stent when drug delivery is desired are polyethylene oxide, polyvinyl pyrrolidone, polyacrylates, and their blends or copolymers or lightly crosslinked forms. Polyethylene glycol block copolymer with polylactides or other polyesters are examples. Hydrophilic polyurethane, poly(maleic anhydride-alt-ethylene) and their derivatives are examples. Other materials are polysaccharides and their derivatives. There are also sodium alginate, karaya gum, gelatin, guar gum, agar, algin carrageenans, pectin, locust bean gums, xanthan, starch-based gums, hydroxy alkyl and ethyl ethers of cellulose, sodium carboxymethyl cellulose. Some of the materials will be heated, then cooled, then a gel is formed. Some of the above are food gels. Some of them are bioadhesives.

Any drugs may be used, singly or in combination. For example, the drugs can be an anticoagulant, e.g. D-Phe-ProArg chloromethyl ketone. An RGD peptide-containing compound, heparin, antithrombin compounds, platelet receptor antagonists, antibodies, aspirin, urokinase, protaglandin inhibitors, platelet inhibitors, or antiplatelet peptide. The drug can be an inhibitor of vascular cell growth, DNA, RNA, cholesterol-lowering agents, vasodilating agents. The drug can be any drug such as Taxol, 5-Fluorouracil, Beta-Estradiol, Tranilast, Trapidil, Probucol, Angiopeptin or any combination of them.

Since there are many drugs and many polymers, the stent can have multiple layers of different polymers with the same or different drugs. For example, the stent can have two layers of the same polymer coating 18 with one layer with drug and another layer without drugs. The stent may have two layers of the same polymer with two different drugs as another example.

In particular, various combinations of a cycling sinase inhibitor identified as p21 and the vascular endothelial growth factor identified as VEGF, an endothelial nitrogen, may preferably be included in and dispensed from the coating polymer layer of a stent.

Incorporation of drugs and growth factors into a polymer layer can also be performed by several other methods, including the solvent method, melting method, soaking method and spraying method. If both polymer and drug have a cosolvent, a solution case will be an easy way to provide the polymer matrix loaded with the drug or growth factor. If the polymer can be melted at low temperature and the drug or growth factor tolerates heating, a melting method can be used to mix the drug or growth factor into the polymer matrix. Also, a polymer-drug solution or suspension solution can be used for coating to provide a layer containing the drug or growth factor.

In another embodiment of the invention the coating may be a film of bioadhesive. Bioadhesives glue body tissue together. Using a bioadhesive for the coating serves two purposes. The stent is smooth and if a tear has occurred the tissue can be repaired. In this manner, blood flow will be maintained in a vessel, for example. The bioadhesive may or may not also have drugs loaded for delivery. Dissection, cutting or tearing occurs in some stent and PTA or PTCA cases. Bioadhesives or surgical adhesives may be used to repair the passage wall. However, these tears or cuts are not necessarily discovered immediately. In those cases, a further medical procedure must be undertaken to repair the wall. The present invention eliminates some of these further medical procedures as a bioadhesive is included in the coating 18 which is delivered when the stent is deployed in place. The bioadhesive will repair damage to the vessel wall and it may not be necessary to undertake a further procedure to do the repair. The bioadhesive is chosen as the coating for the stent or is used in addition to a coating on the stent and is applied in a known manner to one or both ends of the stent. The end or edge, side, outside and/or inside of the stent may utilize the bioadhesive.

Any appropriate bioadhesive may be used. For example, the following bioadhesives may be used singly or in combination:

cyanoacrylate: ethyl cyanoacrylate, butyl cyanoacrylate, octyl cyanoacrylate, hexyl cyanoacrylate;

fibrin glue: fibrinogen/thrombin/Factor XIII/calcium as catalyst gelatin-resorcinol-formol (GRF) glue:

formed from gelatin, resorcinol and water in the presence of formaldehyde, glutaraldehyde and heat (45° C.);

mussel adhesive protein, prolamine gel and transforming growth factor beta(TGF-B);

polyacrylic acid, modified hypromellose, hydroxypropylmethyl cellulose, hydroxypropylcellulose, carboxymethyl cellulose, sodium alginate, gelatin, pectin, polyvinylpylindone, polyethylene glycol, aldehyde relative multifunctional chemicals, polyallylsaccharose, and polypeptides.

Figure 2:
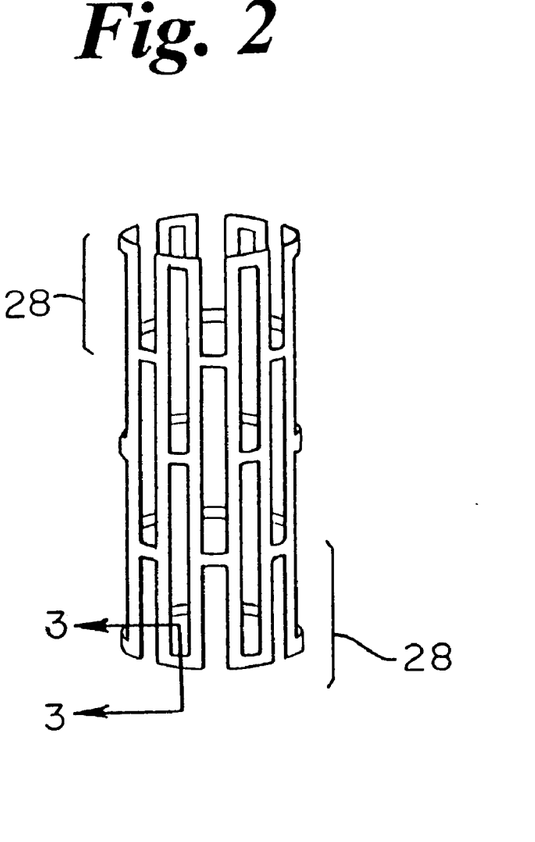
FIG. 2 is a view of another stent according to one embodiment of this invention.
Figure 3:
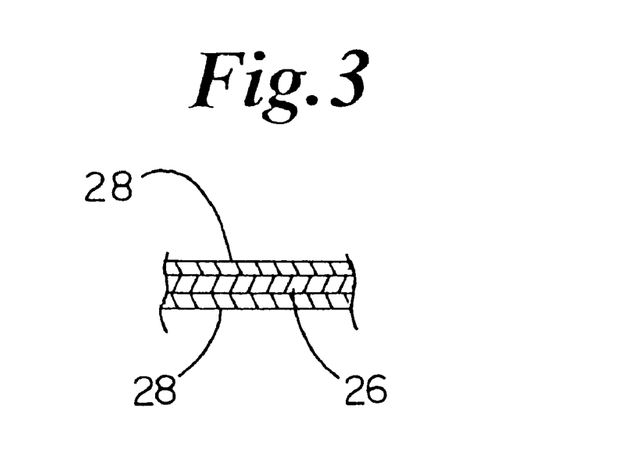
FIG. 3 is a cross sectional view taken along the line 3—3 of FIG. 2.
Figure 4:
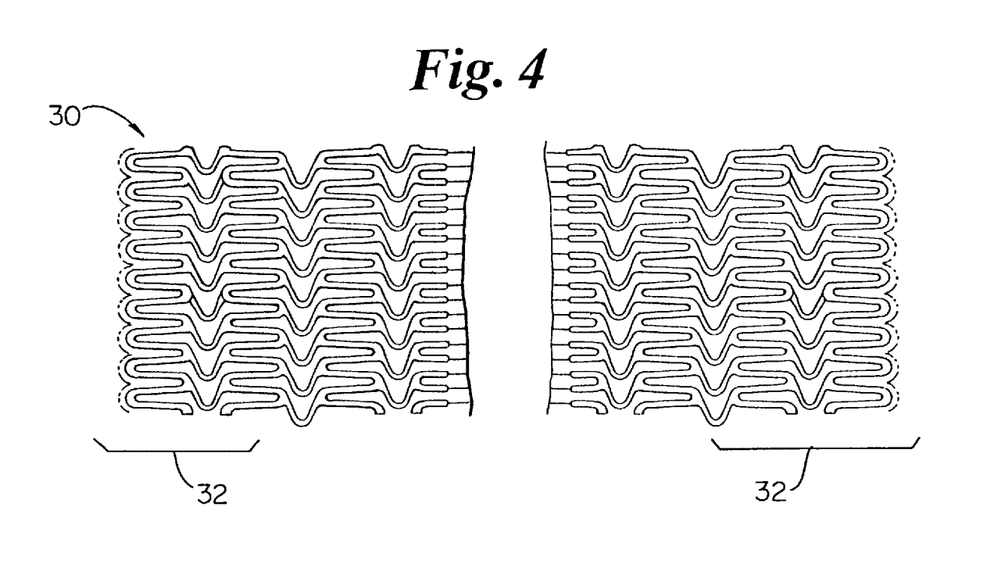
FIG. 4 is fragmentary view of an exemplary representation of a stent configuration, shown in flat plan view, which may be used with this invention.

Referring now to FIGS. 2 and 3, another metal stent is shown. An end portion of stent 26 is coated with a coating 28. Another embodiment of the invention includes a metal stent configuration such as the type shown in part in FIG. 4. Both end portions of stent 30 are coated with a coating 32. These embodiments of FIGS. 2-4 include any appropriate coating utilized as described above and the coating may contain drugs for release and the coating may be a bioadhesive or include a bioadhesive. The stent may be coated on the outer surface only or may be coated on the inner surface as well. The end or edge would also be coated, if desired. One or both ends of the stent may be coated.

It is also contemplated that a stent according to the invention may be of a polymeric material. The stents may be of any configuration and may be of a biodegradable or nonbiodegradable polymeric material. A coating or coatings as described above are utilized on one or both ends of the polymeric stent to reduce injury to body passages and reduce restenosis and possible further medical procedures as described above. The coating may be multiple or single layers and be chosen from a variety of suitable biocompatible coatings. The coating may also include drugs for delivery and/or a bioadhesive may be utilized.

Figure 5:
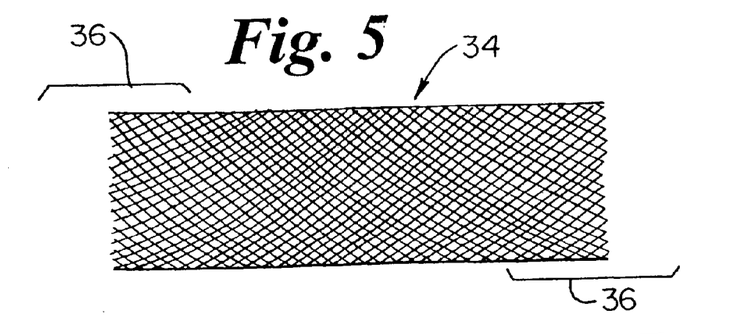
FIG. 5 is an elevational view of one embodiment of a stent according to the present invention.

Another stent is shown in FIG. 5. The stent is generally designated 34. The stent may be composed of a series of strands arranged in a crossing configuration which may be woven, braided or the like or alternatively it may be formed of a polymeric sheet. The end portion of stent 34 includes a coating 36. The coating may be applied by any various standard methods such as dipping, spraying, painting, etc.

Figure 6:
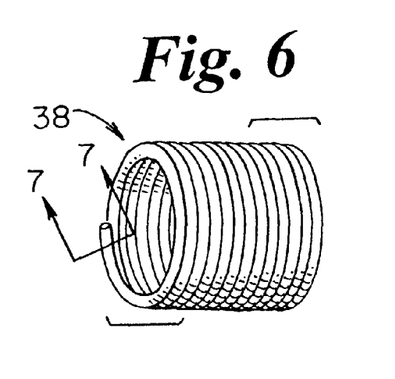
FIG. 6 is a perspective view of another embodiment of a stent in accordance with this invention.
Figure 7:
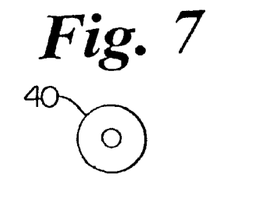
FIG. 7 is a cross section taken along the line 7—7 of FIG. 6.

FIGS. 6 and 7 show yet another stent configuration utilizing a coating on one or both ends. The coil stent 38 includes a coating 40 on both the distal and proximal end portions of the wire member which forms the stent in a preferred embodiment. The appropriate coatings described herein may be utilized with this stent. The coating may be applied to the wire member and then formed or the stent may be formed and lastly, the coating may be applied. Of course, the appearance of both types of stent will differ. One or both end portions may be coated and the coating may be applied to the various areas of the end portions as described earlier.

Figure 8:
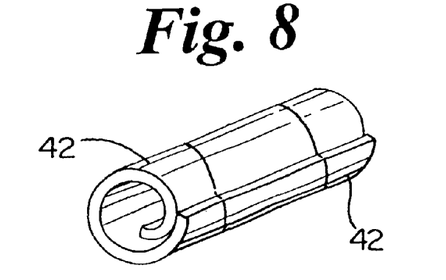
FIG. 8 is a perspective view of yet another embodiment of a stent according to this invention.
Figures 9, 10:
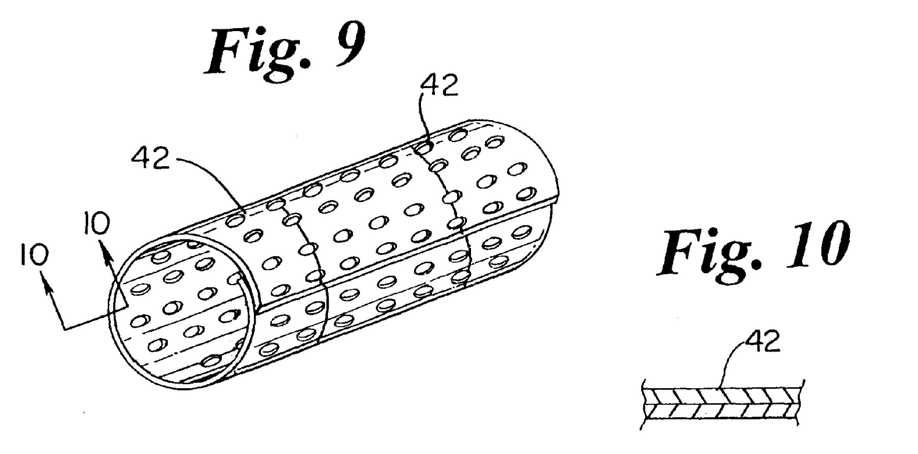
FIG. 9 is a perspective view of a further embodiment of a stent in accordance with this invention.
FIG. 10 is a cross sectional view taken along the line 10—10 of FIG. 9.

FIG. 8 shows yet another stent form, a variation of which is shown in FIGS. 9 and 10, the variation comprising apertures in a sheet like body portion. Both of these stents may be regarded as being formed from a rolled up flat sheet comprised of a metal or a polymeric material having a coating 42 on one or both end portions. The coating 42 is of the type described in this application and may be applied to various areas of the stent as described herein.

Materials suitable for use in forming the polymeric stents to which the invention relates are such that when fabricated to a desired geometry they will afford the stent sufficient strength and support for the particular intended use. Suitable materials do not produce toxic reactions or act as carcinogens. The preferred core polymeric stent materials are those such as are set forth below, which list is not exhaustive but exemplary only: Poly(L-lactide) (PLLA), Poly(D,L-lactide) (PLA), poly(glycolide) (PGA), poly(L-lactide-co-D,L-lactide) (PLLA/PLA), poly(L-lactideco-glycolide) (PLLA/PGA), poly(D,L-lactide-co-glycolide) (PLA/PGA), poly (glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL) and poly(phosphate ester).

Figure 11:
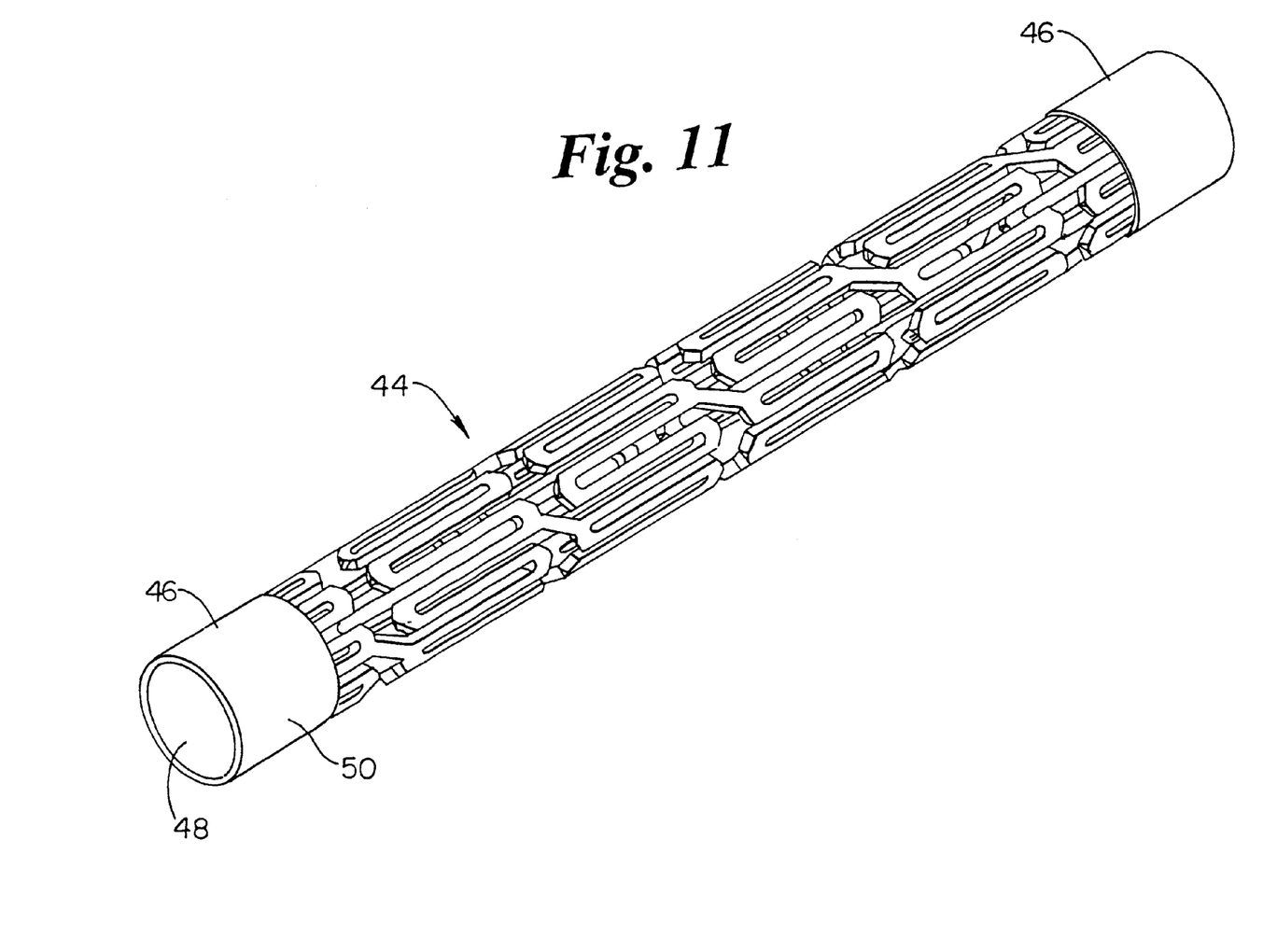
FIG. 11 is a perspective view of another embodiment of the invention utilizing a sleeve.

Referring now to FIG. 11 another stent of the invention is shown. The stent 44 includes at least one sleeve 46 which is designed and configured to fit over the end of a stent. The sleeve 46 is generally hollow like the stent, having a flow passage therethrough. In the preferred embodiment shown, the sleeve is a hollow cylindrical configuration which is connected to overlay the end portion(s) of the stent. The sleeve 46 shown in FIG. 11 overlays both the inside and outside of the stent end when it is attached. The sleeve includes an inner wall 48 and an outer wall 50 having a space therebetween wherein the inner wall 48 is adjacent the inside of the stent and the outer wall 50 is adjacent the outside of the stent. In this manner, the sleeve 46 receives the end of the stent in the space provided between the inner and outer walls. However, it is contemplated that the sleeve could be of a design such that the inner surface of the stent is not covered. The sleeve 46 may also be designed to be slightly longer in length than the stent body so that the sleeve extends beyond the end of the metal or polymeric body. It should also be understood that the sleeve 46 may be of any configuration which will receive the end of any configured stent. Of course, stents of any configuration, shape and materials may be utilized.

The sleeve may be utilized on any stent configuration including, but not limited to, those shown in the figures of this application. The sleeve may be made of any appropriate material as described herein and may include drugs and/or a bioadhesive as discussed above. It should also be understood that it is also contemplated that the sleeve include one or more layers of material including drugs and/or bioadhesives. The materials used may be permanent or biodegradable. It is further contemplated that the sleeve may have a solid wall as shown in FIG. 11 or the wall may be perforated or may be of any design which may or may not coincide with the design of the stent body. The sleeve may be designed to cover various lengths of the stent and if a sleeve is utilized on both ends of the stent they would not necessarily be of the same length.

The sleeve may be bonded to the stent in a number of ways. The sleeve may of a material that has elastic properties so that it will stay in place on the stent end portion. The sleeve may also be bonded to the stent by use of an adhesive. The adhesive would be an appropriate biocompatible adhesive such as those bioadhesives listed earlier in this description, for example, polyurethane and epoxy adhesive. It is also contemplated that the sleeve may be bonded to the stent by the use of heat and pressure. In this manner, the stent will be partially embedded in the sleeve.

Another embodiment of the invention contemplates the use of a metal stent where the stent end or ends have been formed and/or treated so as to be smooth and flexible. Any metal stent may be utilized including but not limited to those shown in FIGS. 1–4. The stent would be manufactured so that the ends would be more flexible and the edges or ends are smoothed to eliminate any sharp edges, jagged areas, or bumps and the like. In order to achieve the additional smoothness the stent may be electropolished and/or tumbled. In this manner, the edges are rounded or smoothed out so that the possibility of damage to a passage is lessened. The stent may also be heat treated to provide improved flexibility in the end portions. The increase in flexibility also decreases the chances of injury to a passage. The stent will bend more easily which will reduce damage which could be caused by a more rigid device. Methods for smoothing articles are known in the art and other appropriate known methods may be used. It is known that heat treating will add flexibility to a metal. Any other method which will provide enhanced smoothness and flexibility to the stent may be utilized.

Figure 12:
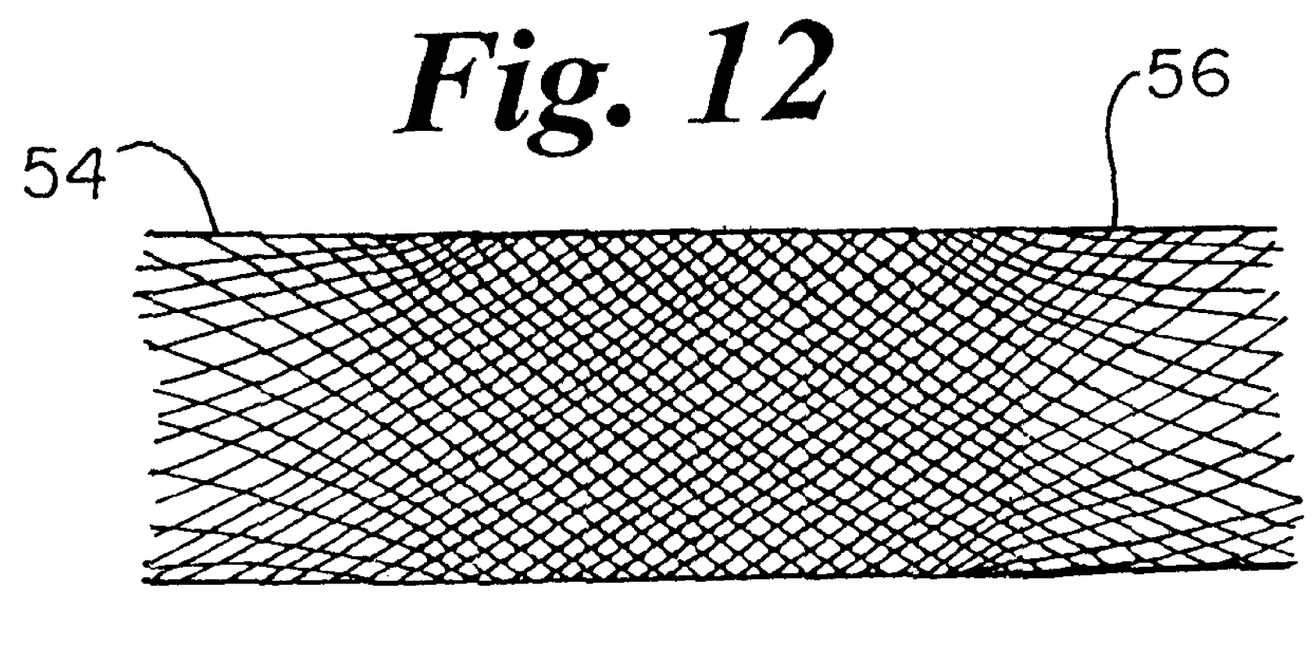
FIG. 12 is an elevational view of another embodiment of a stent according to the present invention.

For example, it is also contemplated that a stent with flexible ends may be provided by utilizing a tighter mesh in the center portion of the stent and a looser mesh on one or both end portions of the stent. Any type of mesh, pattern or braid may be utilized with this embodiment. Such a stent is shown in FIG. 12. The end portions 54 and 56 are of a looser configuration which allows for more flexibility in the end portions. Such a stent may also be treated by methods such as those described above to provide more flexibility and the stent may also be treated to provide for smooth edges or ends. Any stent pattern may be reconfigured to provide for more numerous or tighter struts in the center and less numerous or looser struts on one or both ends.

Another embodiment of a stent in accordance with the invention would include a metal stent which has been treated in accordance with the above methods to be smooth and flexible and then is coated as described earlier in this description.

Yet another embodiment of the invention is a metal stent where different materials of varying flexibility are utilized for portions of the stent body. Such a stent may be configured as shown in FIGS. 1–4 although any stent configuration is appropriate. In a preferred embodiment, such a stent would be of stainless steel in the center portion. The end portions would be of Nitinol, a known nickel and titanium alloy. Nitinol is known to be more flexible than stainless steel. Other appropriate materials may be utilized to provide flexible ends and a more rigid center portion which provides the strength needed in a stent. One or both ends may be of a more flexible material than the center portion. Such a stent may also utilize the above mentioned material treating methods to provide more smooth and flexible ends. For example, if Nitinol ends are utilized, they may be heat treated to add flexibility. Such a stent may also include coated potions as discussed above.

Any of the above described embodiments may be utilized where appropriate in vascular or nonvascular, respiratory, gastrointestinal, rectal, urethral, and vaginal routes.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A stent comprising a main body portion having a first end portion, a second end portion, a middle portion having an outer surface and a flow passage defined therethrough, wherein the first end portion comprises an edge, wherein at least a portion of the edge has a biocompatible coating disposed directly thereon, wherein the biocompatible coating comprises a polymer or a drug, and wherein the middle portion surface is free of the biocompatible coating.

2. The stent of claim 1, wherein the entire edge of the first end portion has the biocompatible coating.

3. The stent of claim 1, wherein the biocompatible coating comprises apertures or perforations.

4. The stent of claim 1, wherein the biocompatible coating comprises a plurality of layers comprising at least one coating material.

5. The stent of claim 4, wherein the plurality of layers is comprised of the same coating material.

6. The stent of claim 4, wherein the plurality of layers is comprised of different coating materials.

7. The stent of claim 1, wherein the polymer is a bioadhesive.

8. The stent of claim 1, wherein the biocompatible coating comprises the polymer and the drug.

9. The stent of claim 8, wherein the polymer comprises a gel-like material.

10. The stent of claim 8, wherein the drug is selected from the group consisting of paclitaxel, an RGD peptide-containing compound, tranilast, trapidil and probucol.

11. The stent of claim 1, wherein the first end portion is more flexible than the middle portion.

12. The stent of claim 1, wherein the first end portion and middle portion are comprised of a mesh, and wherein the mesh of the first end portion is looser than the mesh of the middle portion.

13. A method for manufacturing a stent comprising a main body portion having a first end portion, a second end portion, a middle portion having a surface and a flow passage defined therethrough, wherein the first end portion comprises a surface, and wherein the method comprises treating the surface of the first end portion to form a smooth surface; and applying a biocompatible coating directly to at least a portion of the treated surface of the first end portion, wherein the middle portion surface is free of the biocompatible coating.

14. The method of claim 13, wherein the smooth surface is formed by electro polishing.

15. A method of manufacturing a stent comprising a main body portion having a first end portion having a surface, a second end portion, a middle portion having a surface and a flow passage defined therethrough, wherein the method comprises treating the first end portion surface to form a flexible first end portion; and applying a biocompatible coating directly to at least a portion of the treated surface, wherein the middle portion surface is free of the biocompatible coating.

16. The method of claim 15, wherein the flexible first end portion is formed by heat-treating.

* * * * *